United States Patent [19]

Boxhoorn

[11] Patent Number: 4,874,739
[45] Date of Patent: Oct. 17, 1989

[54] SILVER-CONTAINING CATALYST, PROCESS FOR THE PREPARATION OF THE CATALYST AND THE CATALYST PREPARED BY THE PROCESS

[75] Inventor: Gosse Boxhoorn, Amsterdam, Netherlands

[73] Assignee: Shell Oil Company, Houston, Tex.

[21] Appl. No.: 217,263

[22] Filed: Jul. 11, 1988

[30] Foreign Application Priority Data

Jul. 15, 1987 [GB] United Kingdom ................ 8716653

[51] Int. Cl.$^4$ .......................... B01J 23/04; B01J 23/14; B01J 23/36; B01J 23/50
[52] U.S. Cl. ..................................... 502/218; 502/216; 502/348
[58] Field of Search ................ 502/216, 218, 347, 348

[56] References Cited

U.S. PATENT DOCUMENTS

| | | | |
|---|---|---|---|
| 3,651,167 | 3/1972 | Rosset | 260/681.5 |
| 3,819,537 | 6/1974 | Chan | 252/476 |
| 3,962,136 | 6/1976 | Nielsen et al. | 252/454 |
| 4,092,372 | 4/1978 | Furuoya et al. | 260/681 |
| 4,168,247 | 9/1979 | Hayden et al. | 252/476 |
| 4,207,210 | 6/1980 | Kilty | 252/463 |
| 4,242,235 | 12/1980 | Cognion | 252/455 R |
| 4,356,312 | 10/1982 | Nielsen | 549/534 |
| 4,379,134 | 4/1983 | Weber et al. | 432/626 |
| 4,575,494 | 3/1986 | Young et al. | 502/243 |
| 4,701,437 | 10/1987 | Boxhoorn et al. | 502/348 |
| 4,761,394 | 8/1988 | Lauritzen | 502/348 |
| 4,783,437 | 11/1988 | Boxhoorn | 502/348 |

FOREIGN PATENT DOCUMENTS

| | | |
|---|---|---|
| 0091165 | 10/1983 | European Pat. Off. . |
| 0207542 | 1/1987 | European Pat. Off. . |
| 0226234 | 6/1987 | European Pat. Off. . |
| 1133484 | 11/1968 | United Kingdom . |
| 1413251 | 11/1975 | United Kingdom . |
| 2005262 | 4/1979 | United Kingdom . |
| 1560480 | 2/1980 | United Kingdom . |

*Primary Examiner*—W. J. Shine

[57] ABSTRACT

A process for the preparation of a silver-containing catalyst suitable for the oxidation of ethylene to ethylene oxide which comprises:

(a) mixing alumina with a tin compound and with an alkali metal compound,
(b) calcining the mixture to obtain an alkali metal-enriched and tin-modified alumina carrier,
(c) impregnating the carrier with a solution of a silver compound, which is sufficient to cause precipitation on the carrier of from 1 to 25 prer cent by weight, on the total catalyst, of silver and before, during or after that impregnation also impregnating the carrier with one or more dissolved alkali metal compounds and with a rhenium compound as promoters,
(d) precipitating the sliver compund on the carrier and
(e) reducing the silver compound to metallic silver.

30 Claims, No Drawings

SILVER-CONTAINING CATALYST, PROCESS FOR THE PREPARATION OF THE CATALYST AND THE CATALYST PREPARED BY THE PROCESS

FIELD OF THE INVENTION

The invention relates to a process for the preparation of a silver-containing catalyst, suitable for the preparation of ethylene oxide, to the prepared catalyst and to the use of the catalyst for the preparation of ethylene oxide and the ethylene oxide.

BACKGROUND OF THE INVENTION

It is generally known for a silver-containing catalyst to be employed in the preparation of ethylene oxide. See for example British patent specification 1,413,251 and also the literature cited therein. In order to obtain improved silver catalysts, efforts have been directed for many years towards modifying the silver catalysts with the aid of promoters. For example, the above-mentioned British patent specification 1,413,251 describes a process in which a silver compound is applied to a carrier, after which the applied silver compound is reduced to silver and in which additionally a promoter in the form of potassium oxide, rubidium oxide or cesium oxide or a mixture thereof is present on the carrier.

Applicant has found a silver catalyst with improved selectivity and a high stability and activity.

SUMMARY OF THE INVENTION

The invention relates to a process for the preparation of a silver-containing catalyst suitable for the oxidation of ethylene to ethylene oxide which comprises
 (a) mixing alumina with a tin compound and with an alkali metal compound,
 (b) calcining the mixture to obtain an alkali metal-enriched and tin-modified alumina carrier,
 (c) impregnating the carrier with a solution of a silver compound, which is sufficient to cause precipitation on the carrier of from 1 to 25 per cent by weight, on the total catalyst, of silver and before, during or after that impregnation also impregnating the carrier with one or more dissolved alkali metal compounds and with a rhenium compound as promoters,
 (d) precipitating the silver compound on the carrier and
 (e) reducing the silver compound to metallic silver.

DESCRIPTION OF THE ILLUSTRATIVE EMBODIMENTS

The aluminium oxides can be several modifications of aluminum oxide, such as gamma-aluminum oxide, which when calcined at a final temperature between 1200° C. and 1700° C. generally produce alpha-aluminum oxide. Another possibility is to choose a hydrated aluminum oxide, such as boehmite, which via gamma-aluminum oxide produces alpha-aluminum oxide.

The alkali metal compounds, used for mixing with the aluminum oxide and the tin compound in order to prepare an alumina carrier, comprise alkali metal hydroxides and alkali metal salts, such as fluorides, nitrates, chlorides or sulphates. Preferably potassium, rubidium or cesium compounds are used, most preferably cesium compounds, e.g. cesium chloride, cesium fluoride or cesium sulphate. Mixtures of salt or hydroxides of different alkali metals may also be used.

The quantity of alkali metal compound that is mixed with the alumina is chosen in such an amount, that the atom ratio of the alkali metal/aluminum is between 0.0001 and 0.1, preferably between 0.001 and 0.01.

Examples of tin compounds are tin oxides or tin salts, such as stannic chloride, stannic bromide, stannic fluoride, stannic iodide, stannic nitrate, stannic sulphate, stannic tartrate, stannic chromate. Salts of divalent tin may be suitable as well, e.g. stannous sulphate. Stannic sulphate and stannous sulphate are the most preferred. Stannates could also be used.

The quantity of tin compound that is mixed with the alumina is chosen in such an amount, that the atom ratio of the tin/aluminum is between 0.001 and 0.1, preferably between 0.005 and 0.05.

It has been found that the Sn/Al atom ratio and the Cs/Al atom ratio at the surface of the carrier is greater than the weighed-out Sn/Al and Cs/Al atom ratios respectively. It has further been found that the tin particles at the surface of the carrier have a great influence on the distribution of the metallic silver over the surface, after impregnation of the carrier with the silver compounds and subsequent reduction of the silver compounds.

Scanning electron microscopy revealed that the silver particles on the carrier surface were invisible and could not be detected apartly, which is in contrast to silver particles of a commercial catalyst, which particles could be seen and had a diameter of about 0.2–0.5 $\mu m$. One could also speak of a silver mirror on the surface of the carrier in the catalyst according to the invention.

It should be clear that alkali metals may be present in the alumina before the mixing of any compound, since in the raw alumina materials and ores the aluminum contains impurities of this kind. Substantial amounts, up to 10,000 ppm wt of alkali metals are not unusual. These amounts are neglected in calculations. When alkali is mixed with alumina, we say that the alumina is then "enriched". In the case of tin, which we consider not to be present in the alumina before mixing, we use the term "modified".

For the preparation of the alkali metal-enriched and tin modified alpha-alumina carrier, preferably alumina is mixed with water, the tin compound and the alkali metal compound, and the resulting mixture is extruded to shaped carrier particles, which latter are calcined. The calcination can take place in one or more steps, depending on the choice of starting material. In general, sufficient water is added to make the mixture extrudable. The extrudable paste obtained is then extruded in an extruder to form shaped pieces. These shaped pieces are heated, during which water still present is evaporated. The solid pieces are then calcined. In order to prepare the alpha aluminium oxide modification, calcination up to a temperature of between 1200° C. and 1700° C. is necessary. Suitable starting materials are powders of gamma-aluminium oxide, alpha-aluminium oxide monohydrate, alpha-aluminium oxide trihydrate and beta-aluminium oxide monohydrate, which are sintered during the calcination, with fusion of the powder particles taking place. The heating and calcination also changes the crystal structure: the cubic structure of gamma aluminium oxide changes into the hexagonal structure of alpha aluminium oxide.

The term "calcination" was originally used in industry for the burning of limestone, consisting for a major part of calcium carbonate, to calcium oxide. By way of extension the term "calcination" is used in the chemical encyclopedias in the preparation of alpha-alumina. The term is now generally used in catalyst chemistry.

The effective catalyst surface area can vary from between 0.1 and 5 m$^2$/g, preferably between 0.2 and 2 m$^2$/g. Shaped particles of alpha-alumina comprise i.e. bars, rings, pellets, tablets and triangles. They are especially suitable in fixed bed applications.

In order to prepare the catalyst, the alkali enriched and tin modified alumina carrier is impregnated with a solution of a silver compound, sufficient to apply, as wished, 1 to 25 weight per cent of silver, calculated on the weight of the total catalyst, on the carrier. The impregnated carrier is separated from the solution, if necessary, and the silver compound is precipitated on the surface and the precipitated silver compound is reduced to metallic silver. It may be that the whole solution is impregnated on the carrier. The silver is thus on the surface of the carrier.

Also a promoter is present on the surface of the carrier, for example one or more alkali metals: for example potassium, rubidium or cesium. The promoters can be applied on the carrier before, during or after the impregnation with the silver compound. The promoter can also be applied on the carrier after the silver compound has been reduced to silver. The silver and the promoter are on the surface of the alumina carrier and exercise their catalytic action there.

One or more of the alkali metals potassium, rubidium and cesium, preferably in the form of their salts or hydroxides is added to the silver solution as a promoter. Although the metals potassium, rubidium and cesium exist in pure metal form, they are in that form not suitable for use. Therefore they are administered in a solution of their salts or hydroxides. The amount of added promoter generally lies between 10 and 3000 parts by weight of potassium, rubidium or cesium metal per million parts by weight of total catalyst. Preferably amounts between 250 and 1000 parts by weight are present on the total catalyst.

The alumina carrier is also impregnated with a solution of a rhenium compound. This may be done the same time that this promoter is added, before or later. The amount of rhenium, calculated as the metal, brought on the alumina carrier is between 40 and 2000 parts, preferably between 100 and 1000 parts, by weight per million parts by weight of total catalyst.

Preferably the rhenium compounds used in the preparation of the catalyst according to the invention are the rhenium salts, the rhenium oxides, the rhenium oxyhalides, the perrhenates and the rhenium acids.

As rhenium salts may be mentioned rhenium halides, such as rhenium tetrafluoride, rhenium hexafluoride, rhenium trichloride, rhenium pentachloride, rhenium tribromide; other salts are for example sulphates.

As oxides of rhenium may be mentioned rhenium sesquioxide (Re$_2$O$_3$), rhenium dioxide (ReO$_2$), rhenium trioxide (ReO$_3$) and rhenium heptoxide (Re$_2$O$_7$). Of the perrhenates used in the process according to the invention especially ammonium perrhenate is suitable. However, the alkali metal perrhenates, alkaline earth metal perrhenates, silver perrhenate and other perrhenates can be suitably utilized.

With the rhenium compound also a sulphur compound may be used. It is preferred to use a combination of said compounds. The sulphur compound is preferably added in the form of ammonium sulphate, but other sulphur compounds may be used as well, such as sulphonates, thiols, dimethyl sulphoxide, sulphates, sulphites or thiosulphates.

The rhenium compound (calculated as the metal) in the catalyst is preferably used in an amount of between 40 and 2000 parts by weight per million parts by weight of total catalyst. The sulphur is preferably used in equimolar amounts with respect to the rhenium, but somewhat higher and somewhat lower amounts of sulphur are not excluded.

Preferably as a sulphur compound a sulphate is applied, more preferred ammonium sulphate is applied.

It has been found that sulphate ions are present on the carrier in an amount between 20 and 1000 parts by weight per million parts by weight of total catalyst.

In general, the alumina carrier is generally mixed with an aqueous solution of a silver salt or a silver complex, so that the carrier is impregnated with this solution, after which the carrier may be separated from the solution if necessary and subsequently dried. The impregnated carrier is then heated to a temperature of between 100° C. and 400° C. for a period necessary for the silver salt (or complex) to decompose and form a finely distributed layer of metallic silver which adheres to the inner and outer surfaces of the alumina carrier. Temperatures above 400° C. during long times should be avoided, since then sintering of the silver particles takes place.

Various methods are known for adding the silver. The carrier can be impregnated with an aqueous solution of silver nitrate, then dried, after which the silver nitrate is reduced with hydrogen or hydrazine. The carrier can also be impregnated with an ammoniacal solution of silver oxalate or silver carbonate, the deposition of silver metal being effected by thermally decomposing the salt. Special solutions of silver salt with certain solubilizing and reducing agents, such as combinations of vicinal alkanolamines, alkyldiamines and ammonia also serve the purpose.

As has already been explained the effective catalyst surface area can vary between 0.1 and 5 m$^2$/g, dependent on the alpha-alumina carrier used.

Without being bound by any theory the alkali metal promoter serves to neutralize the "acid sites" on the alumina surface, which sites may influence the formation of carbon dioxide from the ethylene oxide prepared.

Consequently alumina with a small surface area will need less alkali metal promoter than an alumina with greater surface area, in order to give the maximum selectivity of the catalyst. Generally the amount of alkali necessary to give the optimum selectivity is proportional with the surface area of the carrier.

Suitable compounds to serve as starting material for the alkali promoters are, for example, nitrates, oxalates, carboxylic acid salts or hydroxides. The most preferred alkali promoter is cesium.

Some excellent methods are known for adding the alkali metals in which these metals can be applied at the same time as the silver. Suitable alkali metal salts are generally salts which are soluble in the silver-depositing liquid phase. Besides the above-mentioned salts, it is also worth mentioning nitrates, chlorides, iodides, bromides, bicarbonates, acetates, tartrates, lactates and isopropoxides. The use of alkali metal salts which react with the silver present in the solution and thus cause silver salts to be prematurely precipitated from an impregnating solution should, however, be avoided. For example, potassium chloride should not be used for impregnating techniques in which an aqueous silver nitrate solution is used, but potassium nitrate can be used instead. Potassium chloride can be suitably used in a process in which an aqueous solution of silver amine complexes, from which no silver chloride will precipitate, is used.

In addition, the amount of alkali metal deposited on the carrier can be adjusted within certain limits by washing out a part of the alkali metal with, preferably, anhydrous methanol or ethanol. This method is employed subsequently if the concentration of the applied alkali metal is found to be too high. The temperatures, contact times and the drying with gases can be adjusted. Care should be taken to ensure that no traces of alcohol remain in the carrier. Alternatively, a high temperature treatment can be used to inactivate excess alkali metal.

A preferably employed process consists of the carrier being impregnated with an aqueous solution containing both alkali metal salt and silver salt, the impregnating solution being composed of a silver salt of a carboxylic acid, an organic amine, a salt of potassium, rubidium or cesium and an aqueous solvent. For example, a potassium-containing silver oxalate solution can be prepared in two ways. Silver oxide can be reacted with a mixture of ethylene diamine and oxalic acid, giving a solution containing a silver oxalate ethylene diamine complex, to which a certain amount of potassium and possibly other amines such as ethanolamine is added. Silver oxalate can also be precipitated from a solution of potassium oxalate and silver nitrate, the silver oxalate thus obtained then being repeatedly washed in order to remove the attached potassium salts until the desired potassium content is obtained. The potassium-containing silver oxalate is then solubilized with ammonia and/or amine. Solutions containing rubidium and cesium can also be prepared in this way. The thus impregnated carriers are then heated to a temperature of between 100° C. and 400° C., preferably between 125° C. and 325° C.

It is even more preferred to apply all the promoters together with the silver compound in a solution to the alumina carrier.

It should be noted that, irrespective of the nature of the silver in the solution before the precipitation onto the carrier, reference is always made to reduction to metallic silver, whereas it could also be referred to as decomposition on heating. It is preferred to think in terms of reduction, since positively charged Ag ions are converted into metallic Ag. The reduction times can be simply adapted to the starting materials employed.

As mentioned above, a promoter is preferably added to the silver. Cesium is the most preferred promoter in view of the fact that its selectivity for ethylene oxide has been found to be the highest in comparison with the use of potassium or rubidium as promoter.

The invention further relates to a silver-containing catalyst, suitable for use in the oxidation of ethylene to ethylene oxide comprising
(a) an alkali enriched and tin modified alpha-alumina carrier;
(b) from 1 to 25 per cent by weight of metallic silver, based on the weight of the total catalyst on the surface of the carrier,
(c) an alkali metal in an amount between 10 and 3000 parts by weight per million parts by weight of the total catalyst as promoter, and
(d) rhenium in an amount between 40 and 2000 parts by weight per million parts by weight of the total catalyst as additional promoter.

Preferably the catalyst contains between 250 and 1000 ppm of alkali metal, preferably potassium, rubidium or cesium on the surface of the carrier. Preferably the amount of rhenium is between 100 and 1000 ppm. If desired the catalyst may also comprise sulphate-ions on the surface of the carrier. Preferably the alpha-alumina carrier comprises cesium.

The silver catalysts prepared by the process according to the present invention appear to be particularly stable catalysts for the direct catalytic oxidation of ethylene to ethylene oxide with the aid of molecular oxygen. The conditions for carrying out the oxidation reaction in the presence of the silver catalysts according to the invention are fairly similar to those already described in the literature. This applies to, for example, suitable temperatures, pressures, residence times, diluents such as nitrogen, carbon dioxide, steam, argon, methane or other saturated hydrocarbons, the presence or absence of moderating agents to control the catalytic action, for example 1,2-dichloroethane, vinyl chloride or chlorinated polyphenyl compounds, the desirability of employing either recirculating treatments or successive conversions in different reactors to enhance the yield of ethylene oxide, as well as any other special conditions which may be chosen for processes for the preparation of ethylene oxide. Usually, the pressures employed vary from about atmospheric pressure to about 35 bar. Higher pressures are, however, by no means excluded. The molecular oxygen employed as reactant can be obtained from conventional sources. The oxygen feed can consist of substantially pure oxygen, of a concentrated oxygen stream consisting of a large amount of oxygen with smaller amounts of one or more diluents, such as nitrogen, argon, etc., or of another oxygen-containing stream, such as air.

In a preferably employed application of the silver catalysts according to the present invention, ethylene oxide is prepared by contacting an oxygen-containing gas that has been separated from air and that contains not less than 95% oxygen with ethylene in the presence of the catalysts in question at a temperature within the range of 210° C. to 285° C. and preferably between 225° C. and 270° C.

In the reaction of ethylene with oxygen to ethylene oxide, the ethylene is present in at least a double molecular quantity, but the quantity of ethylene employed is often higher. The conversion is therefore calculated according to the quantity of converted oxygen in the reaction and we therefore speak of oxygen conversion. This oxygen conversion is dependent on the temperature of the reaction and is a measure of the activity of the catalyst. The values $T_{30}$, $T_{40}$ and $T_{50}$ refer to the temperatures at 30 mol %, 40 mol % and 50 mol % conversion respectively of the oxygen in the reactor. The temperatures are generally higher for a higher conversion and are highly dependent on the catalyst employed and the reaction conditions. In addition to these T-values, one also comes across selectivity values, which indicate the molar percentage of ethylene oxide in the reaction mixture obtained. The selectivity is indicated as $S_{30}$, $S_{40}$ or $S_{50}$, which refers to the selectivity at 30%, 40% or 50% oxygen conversion respectively.

The concept "stability of a catalyst" cannot be expressed directly. Stability measurements require trials of long duration. For measuring the stability, the applicant has a number of tests which are carried out under extreme conditions with space velocities of 30,000 liter. (liter catalyst)$^{-1}$.h$^{-1}$, where liters of throughput gas are understood to be liters STP (standard temperature and pressure). This space velocity is many times higher than the space velocity in commercial processes, which may range from 2800 to 8000 h$^{-1}$. The test is carried out for at least 1 month. The above-mentioned T- and S-values are measured during the entire period of the test. After the test has been broken off, the total quantity of ethylene oxide per ml catalyst is determined. The difference in selectivity and activity is calculated for a catalyst which would have produced 1000 gram ethylene oxide per ml catalyst. A new catalyst is considered to be more stable than a known catalyst if the differences in the T- and S-values of the new catalyst are less than those of the standard catalyst which is present during each test. The stability tests are carried out at 35% oxygen conversion.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The present invention will now be illustrated by means of the following examples which are provided for illustration and are not to be construed as limiting the invention.

EXAMPLE 1

84.2 g stannosulphate and 35.7 g cesiumfluoride dissolved in 2850 ml water was mixed with 2638.5 g Kaiser aluminium oxide ($Al_2O_3.H_2O$) by adding the stannosulphate-cesiumfluoride aqueous solution to the aluminium oxide during 2 min, and the mixture was kneaded for 30 min in a masticator and extruded. The resulting shaped pieces were dried for 12 hours at 120° C. and subsequently calcined at progressively higher temperatures. Calcination was started with the temperature rising at a rate of 200° C./h to 500° C. Calcination was continued for 1 hour at 500° C., after which the temperature was raised in 2 hours to 1600° C. and continued for 6 hours at 1600° C. The pore volume of the shaped aluminium oxide pieces was 0.55 ml g$^{-1}$ and the average pore diameter was 2.6 μm. The weighed-out cesium-/aluminium atom ratio was 0.006, the weighed-out tin-/aluminium atom ratio was 0.01.

The resulting shaped pieces were impregnated with an aqueous solution of silver oxalate, to which cesium hydroxide, ammonium perrhenate and ammonium sulphate were added. The impregnation was carried out for 10 min under vacuum, after which the shaped pieces were separated from the aqueous solution and placed in a hot air stream at a temperature of 250°–270° C. for 10 min in order to convert the silver salt to metallic silver. The aqueous solution of silver oxalate used was a 28% wt Ag-containing aqueous solution in which the silver oxalate was complexed with ethylene diamine.

The catalyst particles contained 24.2 per cent by weight of silver, 420 ppm of cesium and 1 micromol (186 microgram) rhenium and 1 micromol (32 microgram) sulphur per g catalyst.

The silver catalyst was employed in the preparation of ethylene oxide from ethylene and oxygen. A cylindric steel reactor with a length of 40 cm and a diameter of 5 mm was completely filled with crushed catalyst particles of about 1 mm. The reactor was placed in a bath of silica and alumina particles in fluid bed state. A gas mixture of the following composition was introduced into the reactor: 30 mol % ethylene, 8.5 mol % oxygen, 7 mol % carbon dioxide and 54.5 mol % nitrogen and 5.5 ppm vinyl chloride as moderator. The GHSV was 3300 h$^{-1}$. The pressure was maintained at 15 bar and the temperature dependent on the oxygen conversion.

Measuring-instruments were connected to the reactor and to a computer, such that conversion and reaction temperature could be precisely regulated. With the aid of gas chromatography and mass spectroscopy the amounts of reaction products were determined. The oxygen conversion was 40%.

The selectivity ($S_{40}$) of the above-mentioned silver catalyst was 81.6%, while the oxygen conversion temperature ($T_{40}$) was 242° C. The catalyst showed improved stability.

EXAMPLE 2

84.2 g stannosulphate and 17.86 g cesiumfluoride dissolved in 2750 ml water was mixed with 2638.5 g Kaiser aluminium oxide ($Al_2O_3.H_2O$) by adding the stannosulphate-cesiumfluoride aqueous solution to the aluminium oxide during 2 min, and the mixture was kneaded for 30 min in a masticator and extruded. The resulting shaped pieces were dried for 12 hours at 120° C. and subsequently calcined at progressively higher temperatures. Calcination was started with the temperature rising at a rate of 200° C./h to 500° C. Calcination was continued for 1 hour at 500° C., after which the temperature was raised in 2 hours to 1600° C. and continued for 6 hours at 1600° C. The pore volume of the shaped aluminium oxide pieces was 0.59 ml g$^{-1}$ and the average pore diameter was 2.4 μm. The weighed-out cesium/aluminium atom ratio was 0.003, the weighed-out tin/aluminium atom ratio was 0.01.

The resulting shaped pieces were impregnated with an aqueous solution of silver oxalate, to which cesium hydroxide, ammonium perrhenate and ammonium sulphate were added. The impregnation was carried out for 10 min under vacuum, after which the shaped pieces were separated from the aqueous solution and placed in a hot air stream at a temperature of 250°–270° C. for 10 min in order to convert the silver salt to metallic silver. The aqueous solution of silver oxalate used was a 28% wt Ag-containing aqueous solution in which the silver oxalate was complexed with ethylene diamine.

The catalyst particles contained 20.1 per cent by weight of silver, 450 ppm of cesium and 1 micromol (186 microgram) rhenium and 1 micromol (32 microgram) sulphur per g catalyst.

The silver catalyst was employed in the preparation of ethylene oxide from ethylene and oxygen. A cylindric steel reactor with a length of 40 cm and a diameter of 5 mm was completely filled with crushed catalyst particles of about 1 mm. The reactor was placed in a bath of silica and alumina particles in fluid bed state. A gas mixture of the following composition was introduced into the reactor: 30 mol % ethylene, 8.5 mol % oxygen, 7 mol % carbon dioxide and 54.5 mol % nitrogen and 5.5 ppm vinyl chloride as moderator. The GHSV was 3300 h$^{-1}$. The pressure was maintained at 15 bar and the temperature dependent on the oxygen conversion.

Measuring-instruments were connected to the reactor and to a computer, such that conversion and reaction temperature could be precisely regulated. With the aid of gas chromatography and mass spectroscopy the amounts of reaction products were determined. The oxygen conversion was 40%.

The selectivity ($S_{40}$) of the above-mentioned silver catalyst was 81.9%, while the oxygen conversion temperature ($T_{40}$) was 242° C.

I claim:

1. A process for the preparation of a silver-containing catalyst suitable for the oxidation of ethylene to ethylene oxide which comprises:
   (a) mixing alumina with a tin compound and with an alkali metal compound,
   (b) calcining the mixture to obtain an alkali metal-enriched and tin-modified alumina carrier,
   (c) impregnating the carrier with a solution of a silver compound, which is sufficient to cause precipitation on the carrier of from 1 to 25 per cent by weight, on the total catalyst, of silver and before, during or after that impregnation also impregnating the carrier with one or more dissolved alkali metal compounds and with a rhenium compound as promoters,
   (d) precipitating the silver compound on the carrier and
   (e) reducing the silver compound to metallic silver.

2. The process as claimed in claim 1, wherein the alumina is gamma-alumina or boehmite.

3. The process as claimed in claim 1, wherein the alkali metal compound is an alkali metal salt or an alkali metal hydroxide.

4. The process as claimed in claim 1, wherein in step (a) the alkali metal compound is cesium fluoride.

5. The process as claimed in claim 1, wherein the tin compound is a tin salt or tin oxide.

6. The process as claimed in claim 5, wherein the tin compound is stannous sulphate or stannic sulphate.

7. The process as claimed in claim 1, wherein the alkali metal compound is mixed with the alumina in such quantity that the atomic ratio of alkali/aluminum is between 0.0001 and 0.1.

8. The process as claimed in claim 7, wherein the atomic ratio of alkali/aluminum is between 0.001 and 0.01.

9. The process as claimed in claim 1, wherein the tin compound is mixed with the alumina in such quantity that the atomic ratio of tin/aluminum is between 0.001 and 0.1.

10. The process as claimed in claim 9, wherein atomic ratio of tin/aluminum is between 0.005 and 0.05.

11. The process as claimed in claim 1, wherein the calcination under (b) is carried out at a final temperature of between 1200° C. and 1700° C.

12. The process as claimed in claim 1, wherein alumina is mixed with water, the tin compound and the alkali metal compound, the resulting mixture is extruded to shaped carrier particles, which latter are calcined at a temperature between 1200° C. and 1700° C.

13. The process as claimed in claim 1, wherein in step (c) potassium, rubidium and/or cesium is used as the alkali metal promoter.

14. The process as claimed in claim 13, wherein the alkali metal promoter is present on the catalyst in an amount between 10 and 3000 parts by weight per million parts by weight of the total catalyst.

15. The process as claimed in claim 14, wherein the amount of alkali metal promoter is between 250 and 1000 parts by weight per million parts by weight of the total catalyst.

16. The process as claimed in claim 1, wherein the rhenium compound is a rhenium salt or a rhenium oxide.

17. The process as claimed in claim 16, wherein the rhenium salt is a perrhenate.

18. The process as claimed in claim 17, wherein ammonium perrhenate is used.

19. The process as claimed in claim 16, wherein the rhenium salt is rhenium sulphate.

20. The process as claimed in claim 1, wherein the amount of rhenium calculated as the metal, is between 40 and 2000 parts by weight per million parts by weight of total catalyst.

21. The process as claimed in any one of the claims 1–20, wherein in step (c) also a sulphur compound is impregnated on the carrier.

22. A process for the preparation of a silver-containing catalyst suitable for the oxidation of ethylene to ethylene oxide which comprises:
   (a) mixing alumina with water, a tin compound and with an alkali metal compound wherein the atomic ratio of alkali/aluminum is between 0.001 and 0.01 and the atomic ratio of tin/aluminum is between 0.005 and 0.05,
   (b) extruding the mixture to formed shaped carrier particles,
   (c) calcining the carrier at a temperature between 1200° C. and 1700° C.,
   (d) impregnating the carrier with a solution of a silver compound which is sufficient to cause precipitation on the carrier of from 1 to 25 percent by weight, on the total catalyst, of silver and before, during or after that impregnation also impregnating the carrier with one or more dissolved alkali metal compounds and with one or more rhenium compounds as promoters sufficient to deposit between 10 and 3000 parts by weight per million parts by weight of the total catalyst of alkali metal promoter and to deposit between 40 and 2000 parts by weight per million parts by weight of total catalysts of rhenium compound,
   (e) precipitating the silver compound on the carrier and
   (f) reducing the silver compound to metallic silver.

23. The process of claim 22 wherein in step (d) a sulfur compound is impregnated on the carrier.

24. Silver-containing catalyst, whenever prepared by means of a process as claimed in any one of claims 1–20, 22 or 23.

25. A silver containing catalyst suitable for use in the oxidation of ethylene to ethylene oxide, comprising
   (a) an alkali metal-enriched and tin modified alpha-alumina carrier,
   (b) from 1 to 25 per cent by weight of metallic silver, based on the weight of the total catalyst on the surface of the carrier,
   (c) an alkali metal in an amount between 10 and 3000 parts by weight per million parts by weight of the total catalyst as promoter, and
   (d) rhenium in an amount between 40 and 2000 parts by weight per million parts by weight of the total catalyst as additional promoter.

26. The silver-containing catalyst as claimed in claim 25, characterized in that the alkali metal under (a) comprises cesium.

27. The silver-containing catalyst as claimed in claim 25, characterized in that the alkali metal under (c) is potassium, rubidium and/or cesium.

28. The silver-containing catalyst as claimed in any one of the claims 25–27, characterized in that the catalyst contains sulphate ions on the carrier surface.

29. The silver-containing catalyst as claimed in claim 25, characterized in that the alkali-metal under (c) is present in an amount between 250 and 1000 parts by weight per million parts by weight of the total catalyst.

30. The silver-containing catalyst as claimed in claim 25, characterized in that the amount of rhenium (as metal) is between 100 and 1000 parts by weight per million parts by weight of total catalyst.

* * * * *